(12) United States Patent
Slonaker

(10) Patent No.: US 9,639,003 B2
(45) Date of Patent: May 2, 2017

(54) PROGRAMMABLE IMAGING ASSEMBLY FOR MANUFACTURING BIOTEST POST ARRAYS

(71) Applicant: NIKON CORPORATION, Tokyo (JP)

(72) Inventor: Steven Douglas Slonaker, San Mateo, CA (US)

(73) Assignee: Nikon Corporation (JP)

(*) Notice: Subject to any disclaimer, the term of this patent is extended or adjusted under 35 U.S.C. 154(b) by 191 days.

(21) Appl. No.: 14/523,757

(22) Filed: Oct. 24, 2014

(65) Prior Publication Data

US 2015/0116682 A1      Apr. 30, 2015

Related U.S. Application Data

(60) Provisional application No. 61/895,013, filed on Oct. 24, 2013.

(51) Int. Cl.
| | | |
|---|---|---|
| *G03B 27/32* | (2006.01) | |
| *G03B 27/72* | (2006.01) | |
| *G03F 1/00* | (2012.01) | |
| *G03F 7/20* | (2006.01) | |
| *B01L 3/00* | (2006.01) | |
| *G01N 15/00* | (2006.01) | |
| *G01N 15/14* | (2006.01) | |

(52) U.S. Cl.
CPC ........ *G03F 7/70083* (2013.01); *B01L 3/5027* (2013.01); *B01L 3/502707* (2013.01); *G03F 7/7035* (2013.01); *G03F 7/70191* (2013.01); *G03F 7/70283* (2013.01); *G03F 7/70291* (2013.01); *G03F 7/70558* (2013.01); *G03F 7/70583* (2013.01); *G01N 15/1463* (2013.01); *G01N 15/1475* (2013.01); *G01N 2015/0065* (2013.01)

(58) Field of Classification Search
CPC ............. B01L 3/5027; B01L 3/502707; B01L 2300/0819; G01N 15/1463; G01N 15/1475; G01N 2015/0065; G03F 7/70083; G03F 7/70191; G03F 7/70283; G03F 7/70291; G03F 7/7035; G03F 7/70558; G03F 7/70583
USPC ............. 355/37, 71, 77, 78; 422/502; 430/5, 430/322, 325
See application file for complete search history.

(56) References Cited

U.S. PATENT DOCUMENTS

| | | | |
|---|---|---|---|
| 6,271,957 B1 | 8/2001 | Quate et al. | |
| 6,480,324 B2 | 11/2002 | Quate et al. | |
| 2003/0214571 A1* | 11/2003 | Ishikawa | B23K 26/0604 347/255 |
| 2009/0092934 A1* | 4/2009 | Christophersen | G03F 7/70075 430/325 |
| 2012/0170014 A1* | 7/2012 | Odom | G03B 27/54 355/70 |

* cited by examiner

*Primary Examiner* — Colin Kreutzer
(74) *Attorney, Agent, or Firm* — Roeder & Broder LLP; Steven G. Roeder

(57) ABSTRACT

An imaging assembly for directing a pattern of energy at a workpiece includes (i) a reticle that defines a reticle array that includes a plurality of spaced apart, transmitting regions; (ii) an illumination source that generates an illumination beam; and (iii) a director assembly that selectively directs the illumination beam at the reticle array, the director assembly includes a plurality of director elements that are individually controlled to selectively control the beam pattern that is directed at the reticle array.

19 Claims, 6 Drawing Sheets

PROGRAMMABLE IMAGING ASSEMBLY FOR MANUFACTURING BIOTEST POST ARRAYS

CROSS-REFERENCE TO RELATED APPLICATION

This application claims priority on U.S. Provisional Application Ser. No. 61/895,013 filed on Oct. 24, 2013 and entitled "PROGRAMMABLE IMAGING ASSEMBLY FOR MANUFACTURING BIOTEST POST ARRAYS". As far as is permitted, the contents of U.S. Provisional Application Ser. No. 61/895,013 are incorporated herein by reference.

BACKGROUND

BioTest chips are used for a variety of purposes, including disease diagnosis and detection of bioterrorism agents. One type of BioTest chip includes a substrate, and a biosensor array that includes a densely packed, two-dimensional grid of biosensors positioned on the substrate. In certain designs, each individual biosensor in unique in composition.

Unfortunately, it is very difficult to accurately control the composition and position of each unique biosensor in the biosensor microarray. Existing procedures for manufacturing BioTest chips are slow, and as a result thereof, have a low-throughput and high manufacturing cost.

Additionally, in some current BioTest chip manufacturing processes, a unique mask pattern ("reticle") is currently applied in the exposure of perhaps several dozen process layers. The cost of these many masks can be a significant portion of the total manufacturing cost of the BioTest chips.

SUMMARY

The present invention is directed to an imaging assembly for directing a pattern of energy at a workpiece. In one embodiment, the imaging assembly includes (i) a reticle that defines a reticle array that includes a plurality of spaced apart, transmitting regions; (ii) an illumination source that generates an illumination beam; and (iii) a director assembly that selectively directs the illumination beam at the reticle array, the director assembly includes a plurality of director elements that are individually controlled to selectively control the beam pattern that is directed at the reticle array. In certain embodiments, each of the transmitting regions of the reticle has a surface roughness, to enable and ensure the feature of "incoherent imaging".

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
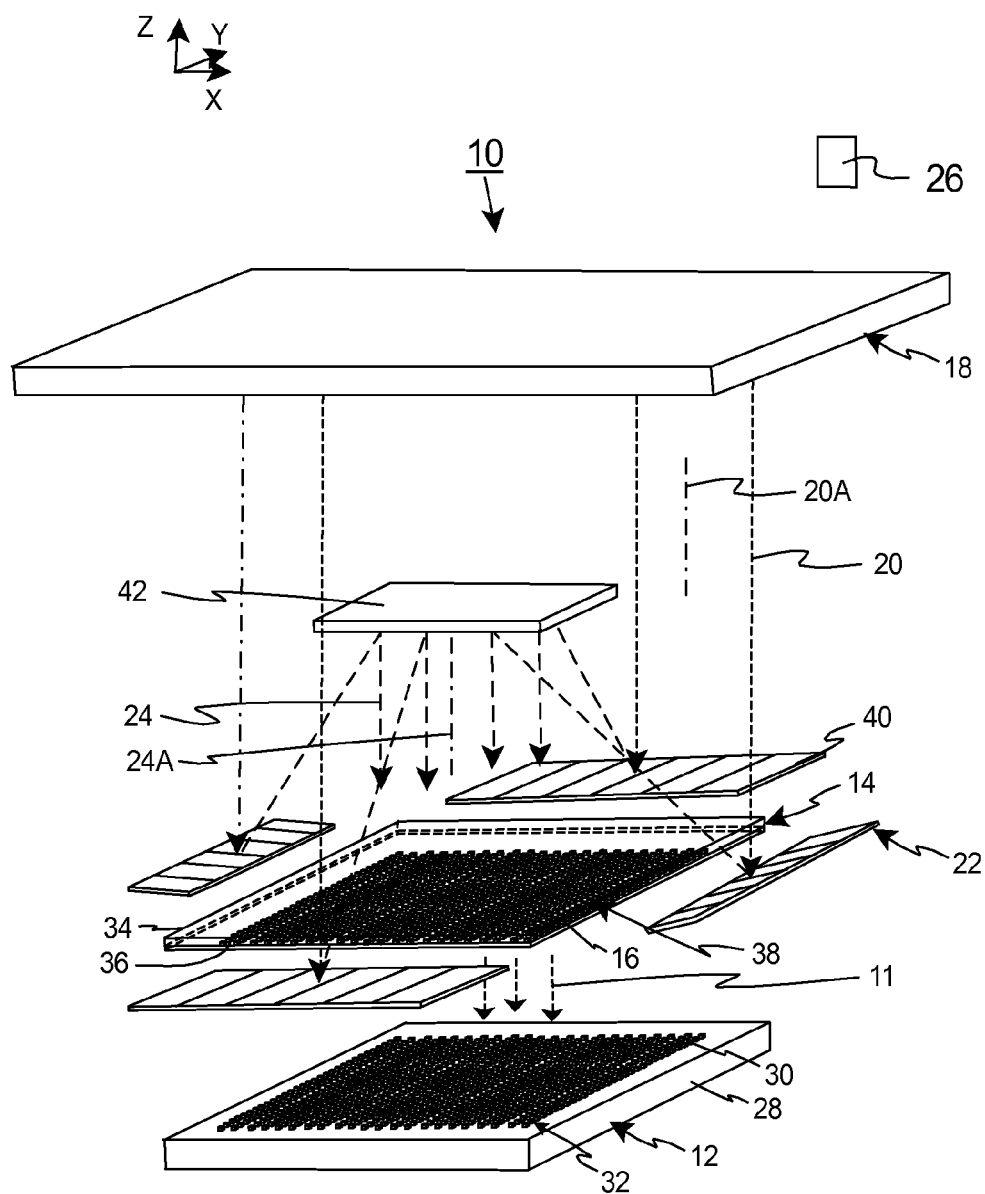
FIG. 1 is a simplified perspective view of an imaging assembly having features of the present invention and a workpiece.

FIG. 1 is a perspective view of an imaging assembly 10 that directs a pattern of energy 11 (illustrated with short dashed arrows) at a workpiece 12. In one embodiment, the imaging assembly 10 includes (i) a fixed reticle 14 (also referred to as a "pixel array reticle" or a "pixel array mask") that includes a plurality of transmitting regions 16; (ii) an illumination source 18 (illustrated as a rectangle) that generates an illumination beam 20 (illustrated with dash dotted arrows); (iii) a director assembly 22 that receives the illumination beam 20 from the illumination source 18, and that directs a shaped illumination beam 24 (Illustrated with long dashed arrows) at the transmitting regions 16; and (iv) a control system 26 (illustrated as a box) that controls the operation of the imaging assembly 10.

Some of the Figures provided herein include an orientation system that designates an X axis, a Y axis, and a Z axis that are orthogonal to each other. In these Figures, the Z axis is oriented in the vertical direction. It should be understood that the orientation system is merely for reference and can be varied. Moreover, these axes can alternatively be referred to as the first, the second, or a third axis.

As an overview, in certain embodiments, the imaging assembly 10 provided herein allows for a customized dose control (via the pattern of energy 11) to be applied to the workpiece 12 to build the workpiece 12. Further, the pattern of energy 11 can be selectively adjusted to provide a plurality of alternative customized doses that are used to build alternative workpiece 12 designs.

The type of workpiece 12 manufactured with the imaging assembly 10 can be varied. In one non-exclusive embodiment, the workpiece 12 is a BioTest chip that includes a substrate 28 (sometimes referred to as a "wafer") and a plurality of posts 30 (e.g. biosensors) that are formed on and that rise substantially perpendicular from the substrate 28. In one embodiment, the posts 30 are densely packed and arranged in a post array 32 (e.g. a biomolecule array).

The number, organization, shape, and composition of the posts 30 can be varied to suit the desired usage of the workpiece 12. As alternative, non-exclusive examples, the workpiece 12 includes approximately ten (10), one hundred (100), one thousand (1000), ten thousand (10000), or one hundred thousand (100000) individual posts 30.

Further, in FIG. 1, the plurality of posts 30 are equally spaced apart and are arranged in a systematic, two dimensional, rectangular shaped, post array 32 that includes a plurality of linear rows and linear columns. Alternatively, for example, the post array 32 can have another configuration, e.g. a linear array of posts 30.

Moreover, in FIG. 1, each of the plurality of posts 30 has a generally rectangular (more specifically, square) shaped cross-section. As alternative, non-exclusive examples, each of the plurality of posts 30 can have a cross-sectional area of approximately one hundred (100) microns, ten (10) microns, one (1) micron, or one tenth (0.1) micron. Further, as alternative, non-exclusive examples, the distance between adjacent posts 30 can be approximately equal to the size of the respective posts or 0.5×, 1.5×, 2×, 5×, or 10× the size of the respective posts. Alternatively, for example, one or more of the posts 30 can have another shape, e.g. a circular shaped cross-section, and/or the spacing between adjacent posts 30 can be different than that provided above.

In one embodiment, the composition of each of the posts 30 in the post array 32 is different and independent. As a result thereof, each of the posts 30 can perform a specific test. Alternatively, in certain embodiments, one or more of the posts 30 can be similar in the post array 32. In one embodiment, one or more of the posts 30 is a biomolecule "post" (e.g. a biosensor), and one or more of the posts 30 includes a plurality of layers of biomolecules that are sequentially added to form the respective post 30. The number and composition of each of the layers can be varied. Therefore, each of the posts 30 can perform a specific test (e.g. screening test, diagnostic test).

As provided above, the imaging assembly 10 allows for a plurality of sequential, customized, patterns of energy 11 to be applied to the workpiece 12 to customize the composition (e.g. layers) of each post 30 built on the substrate 28. The manufacturing of the workpiece 12 is described in more detail below.

The design of the transmission of the reticle 14 can be varied to suit the desired design of the workpiece 12. In FIG. 1, the reticle 14 includes a reticle body 34 that defines a non-transmitting region 36, and the plurality of spaced apart transmitting regions 16. In one embodiment, the reticle 14 is fixed relative to the workpiece 12, and some of the other components of the imaging assembly 10 are moved relative to the reticle 14 and the workpiece 12.

As provided herein, each of the transmitting regions 16 can be referred to as a reticle pixel (or mask pixel). In one embodiment, the number of transmitting regions 16 is greater than or equal to the number of posts 30, and the transmitting regions 16 are arranged in a similar pattern to the posts 30. Stated in another fashion, in one embodiment, the transmitting regions 16 are arranged in a reticle array 38 that is similar to and that corresponds to the post array 32 of the posts 30. For example, in FIG. 1, the plurality of transmitting regions 16 are equally spaced apart and are arranged in a systematic, two dimensional, rectangular shaped, reticle array 38 that includes a plurality of linear rows and linear columns. Alternatively, for example, the reticle array 38 can have another configuration, e.g. a linear array of transmitting regions 16.

Moreover, in FIG. 1, each of the plurality of transmitting regions 16 has a generally rectangular (more specifically, square) shaped cross-section that corresponds to the shape of the biosensors 30. As alternative, non-exclusive examples, each of the plurality of transmitting regions 16 can have a cross-sectional area of approximately 0.1×0.1 micron, 1×1 micron, 10×10 microns, 100×100 microns, or 1000×1000 microns. Further, as alternative, non-exclusive examples, the distance between adjacent transmitting regions 16 is approximately equal to the size of the respective posts, or 0.5×, 1.5×, 2×; 5×, or 10× the size of the respective posts. Alternatively, for example, one or more of the transmitting regions 16 can have another shape, e.g. a circular shaped cross-section, and/or the spacing between adjacent transmitting regions 16 can be different than that provided above. For example, the transmitting regions 16 can have a pre-scribed shaped cross-section that, when imaged by the imaging device, corresponds to the shape of the biosensors 30.

The illumination source 18 generates the illumination beam 20 that directed along an illumination beam path 20A at the director assembly 22. The design of the illumination source 18 can be varied to suit the properties of the materials used on the workpiece 12. In one, non-exclusive embodiment, the illumination source 18 is a Krypton Fluroide "KrF" type illumination system that generates an illumination beam 20 having a center wavelength of approximately two hundred and forty-eight nanometers (248 nm). In this embodiment, the illumination beam 20 serves to excite and propagate a cross-linking of the biomolecule in the coated material with the existing material lying beneath it. Alternatively, the illumination source 18 and/or the wavelength of the illumination beam 20 can be different than that described above. In one embodiment, the illumination beam 20 can be a substantially coherent beam. In one embodiment, the illumination beam 20 can be a pulsed beam.

The director assembly 22 is positioned in the illumination beam path 20A from the illumination source 18, and creates and directs the shaped illumination beam 24 at the reticle array 38 along a shaped beam path 24A. With the present design, the director assembly 22 can be controlled by the control system 26 to selectively and individually control the dose of energy that is directed at each of the transmitting regions 16. Stated in another fashion, the director assembly 22 can be controlled by the control system 26 to individually and selectively direct zero energy or a predetermined amount of energy to each of the transmitting regions independently 16, to selectively and individually not illuminate or illuminate each of the post positions 30.

The design of the director assembly 22 can be varied to suit the requirements of the imaging assembly 10. In one embodiment, the director assembly 22 includes a beam shaper assembly 40 and a beam redirector 42. Alternatively, the director assembly 22 can be designed to include more than one beam shaper assembly 40 and/or more than one beam redirector 42.

The beam shaper assembly 40 receives the illumination beam 20 generated by the illumination source 18 and steers the light (referred to as the shaped illumination beam 24) to the desired transmitting regions 16 of the reticle 14 to expose the desired posts 30. In one embodiment, the beam shaper assembly 40 includes a plurality of individual director elements (e.g. rectangular micromirrors, deflector elements) that are individually controlled (tilted) to selectively control the beam pattern that is directed at the reticle array 16. As an example, the beam shaper assembly 40 can be a MicroElectroMechanical ("MEMS") mirror assembly such as a digital light processing ("DLP") or SLM mirror array. With this design, during the exposure of each layer (e.g. each biomolecular layer), those posts 30 that are designated to not receive light are simply not targeted by any of the individual director elements of the beam shaper assembly 40. Stated in another fashion, with this design, by dynamically controlling the individual director elements, it is possible to steer the direction of light beams to create the shaped illumination beam 20 and the desired dosage of light to each transmitting region 16 and each post 30.

With the combination of the beam shaper assembly 40 and the reticle 14, the beam shaper assembly 40 is used only to control dosage based on how many director elements are pointed at each transmitting region 16 in the pixel array reticle 14. The shape of each transmitting region 16 that receives light from the beam shaper assembly 40 controls the shape of the resulting pattern of energy 11.

The number, shape, and the arrangement of the micromirrors can be varied to achieve the design requirements of the beam shaper assembly 40. In alternative, non-exclusive embodiments, the beam shaper assembly 40 includes approximately ten thousand (10000), one hundred thousand (100000), one million (1000000), or ten million (10000000) individually controllable director elements.

The beam shaper assembly 40 directs the shaped beam 24 at the beam director 42. In one embodiment, the beam director 42 is a mirror that reflects the shaped beam 24 at the reticle array 16 along the shaped beam path 24A.

It should be noted that in certain embodiments, the reticle 14 and workpiece 12 are in a fixed relationship during the exposure of the posts 30. This simplifies the manufacturing process.

The control system 26 is electrically connected to and controls the various components of the imaging assembly 10. For example, the control system 26 can control the position of the individual micromirrors of the beam shaper assembly 40. With this design, the control system 26 can control the beam shaper assembly 40 and resulting tilt angles of the micromirrors, so that light (from the shaped illumination beam 24) fills the selected transmitting regions 16 ("pixels") within the reticle array 38 with the programmed amount of dose.

Figure 2A:
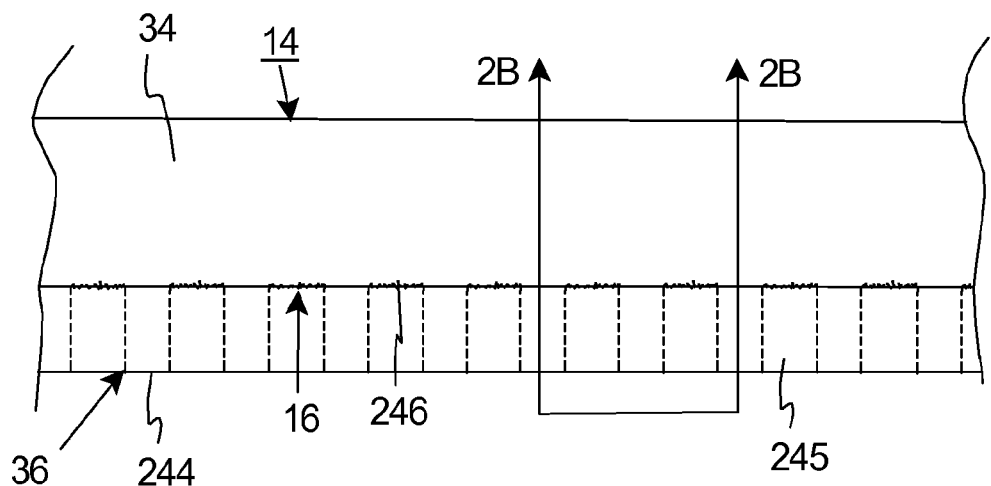
FIG. 2A is an enlarged end view of a portion of a reticle having features of the present invention.
Figure 2B:
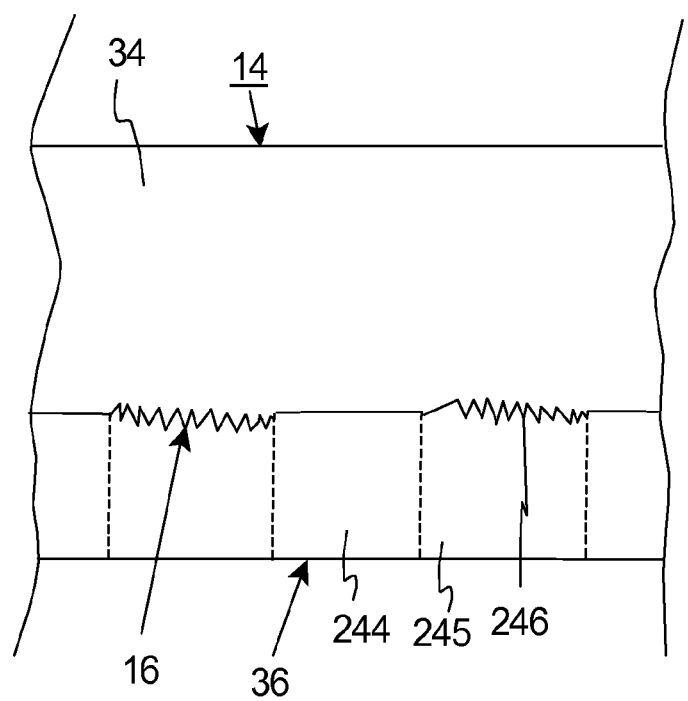
FIG. 2B is an enlarged view taken from FIG. 2A.

FIG. 2A is an enlarged end view of a portion of the reticle 14 of FIG. 1, and FIG. 2B is an enlarged view of the reticle 14 taken from FIG. 2A. In this embodiment, the reticle body 34 is made of a transparent material. As a non-exclusive embodiment, the reticle body 34 can be made of transparent quartz. In one embodiment, the reticle body 34 is generally rectangular shaped, and a bottom side of the reticle body 34 can be covered with a non-transparent layer 244 that defines the non-transmitting region 36 and that includes a plurality of holes/openings 245 (illustrated in phantom) that define the plurality of transmitting regions 16 of the reticle 14. For example, the non-transparent layer 244 can be made of chrome or another suitable material that is deposited on the bottom of the reticle body 34. As provided above, in one embodiment, each transmitting region 16 is generally rectangular shaped.

In one embodiment, the bottom of the reticle body 34, at one or more (e.g. all) of the transmitting regions 16, has been etched, coated or otherwise manufactured to have a high surface roughness 246 to diffuse the beam (not shown in FIGS. 2A and 2B) that is transmitted through the reticle body 34 at the transmitting regions 16. In alternative, non-exclusive embodiments, the surface roughness 246 is at least approximately ten nanometer root mean square (10 nm rms), one hundred nanometer root mean square (100 nm rms), one micron root mean square (1 micron rms), or ten micron root mean square (10 micron rms). Stated in another fashion, in alternative, non-exclusive embodiments, the surface roughness 246 is between approximately (i) ten nanometer root mean square (10 nm rms) and ten micron root mean square (10 micron rms); (ii) one hundred nanometer root mean square (100 nm rms) and ten micron root mean square (10 micron rms; or (iii) one micron root mean square (1 micron rms) and ten micron root mean square (10 micron rms).

With this design, each hole/opening 245 in the non-transparent layer 244 defines one transmitting region 16, and the surface roughness 246 on the output side of reticle body 34 functions as a local diffuser. This has the effect of changing the projection imaging mode to be incoherent. Stated in another fashion, the present invention utilizes the pixel array reticle 14 as an intermediate and incoherent object so that the pattern of energy 11 that leaves the reticle is an incoherent beam. With this design, the surface roughness 246 effectively removes nearly all angular sensitivity to the shaped illumination beam 24. As a result thereof, no matter which director element targets a given transmitting region 16 ("pixel") in the reticle 14, the output intensity distribution of the pattern of energy 11 will be approximately uniform over all output angles. Further, the distribution of the pattern of energy 11 leaving each transmitting region 16 ("pixel") in the reticle 14 will be completely uncorrelated to all other transmitting regions 16, in terms of potential interference effects. Moreover, each separate transmitting region 16 in the reticle 14 is available for independent adjustment of dose, by simply adding director elements to or removing director elements from the population of director elements that are targeted at that particular transmitting region 16 ("pixel") in the reticle 14.

In summary, a coherent shaped illumination beam 24 is converted to an incoherent pattern of energy 11 by the reticle 14.

Figure 3A:
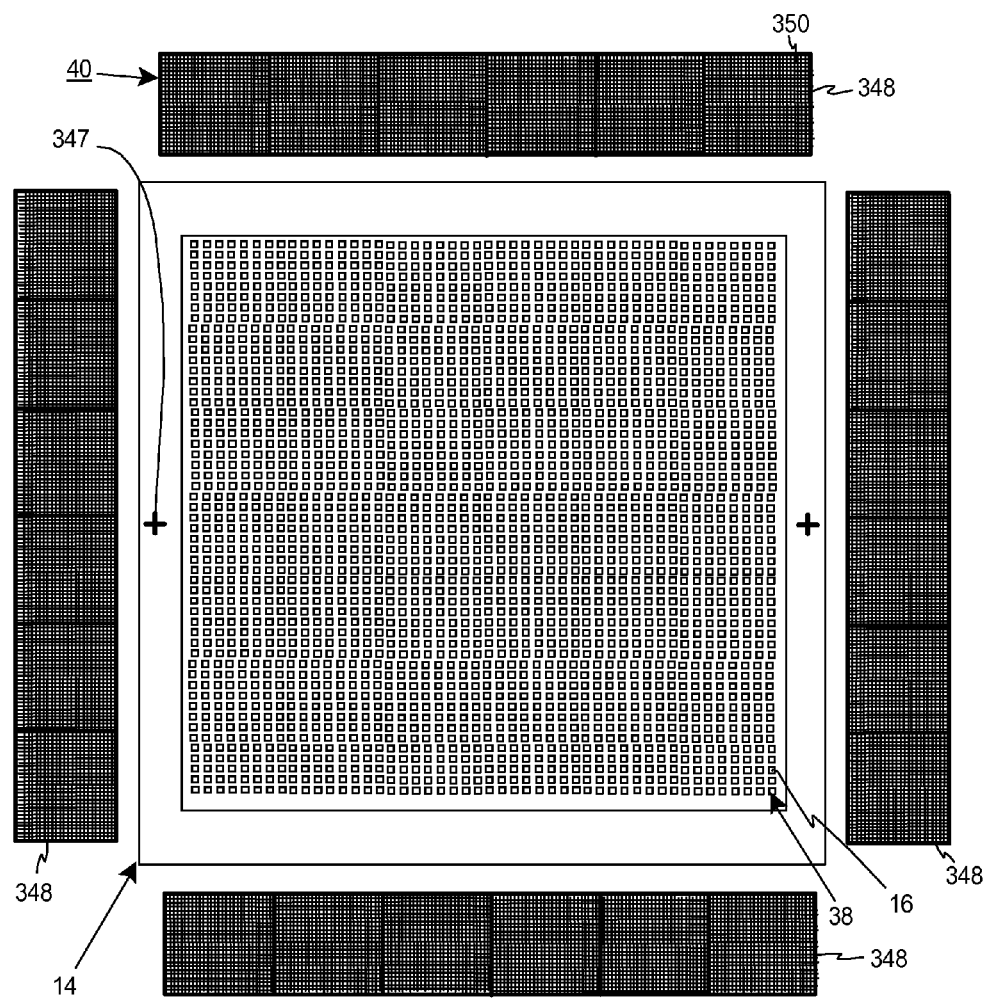
FIG. 3A is a simplified top-down view of the reticle, and the beam shaper assembly.

FIG. 3A is a simplified top-down view of the reticle 14 including the reticle array 38 with the plurality of transmitting regions 16, and the beam shaper assembly 40 that is positioned around and that surrounds the reticle 14. In this embodiment, the reticle 14 includes one or more reticle alignment marks 347 that are used to align the reticle 14.

In this non-exclusive embodiment, beam shaper assembly 40 includes four separate director arrays 348 that are positioned around reticle 14. Alternatively, the beam shaper assembly 40 can include another configuration than illustrated in FIG. 3A.

Moreover, each separate director array 348 includes a plurality of independently controllable director elements 350 (e.g. the micromirrors). It should be noted that the number of director elements 350 in each director array 348 can be varied.

Figure 3B:
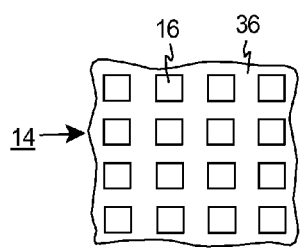
FIG. 3B is an enlarged top view of a portion of the reticle of FIG. 3A.

FIG. 3B is an enlarged top view of a portion of the reticle 14, and illustrates sixteen of the spaced apart, square, transmitting regions 16 and a portion of the non-transmitting region 36 of the reticle 14.

Figure 3C:
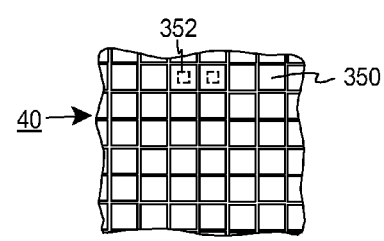
FIG. 3C is an enlarged top view of a portion of the beam shaper assembly of FIG. 3A.

FIG. 3C is an enlarged top view of a portion of the beam shaper assembly 40, and illustrates a plurality of the spaced apart, square, tightly packed, independently controllable director elements 350. Further, a couple of director movers 352 are illustrated in phantom with a box. As provided herein, in certain embodiments, each director element 350 includes a separate, independently controllable director mover 352 that selectively moves or distorts the respective director element 350 to provide the desired shape of the shaped illumination beam 24 (illustrated in FIG. 1).

With this design, referring to FIGS. 3A-3C, each separate transmitting region 16 in the reticle 14 is available for independent adjustment of dose, by simply adding director elements 350 to or removing director elements 350 from the population of director elements 350 that are targeted at that particular transmitting region 16 ("pixel") in the reticle 14.

Figure 4:
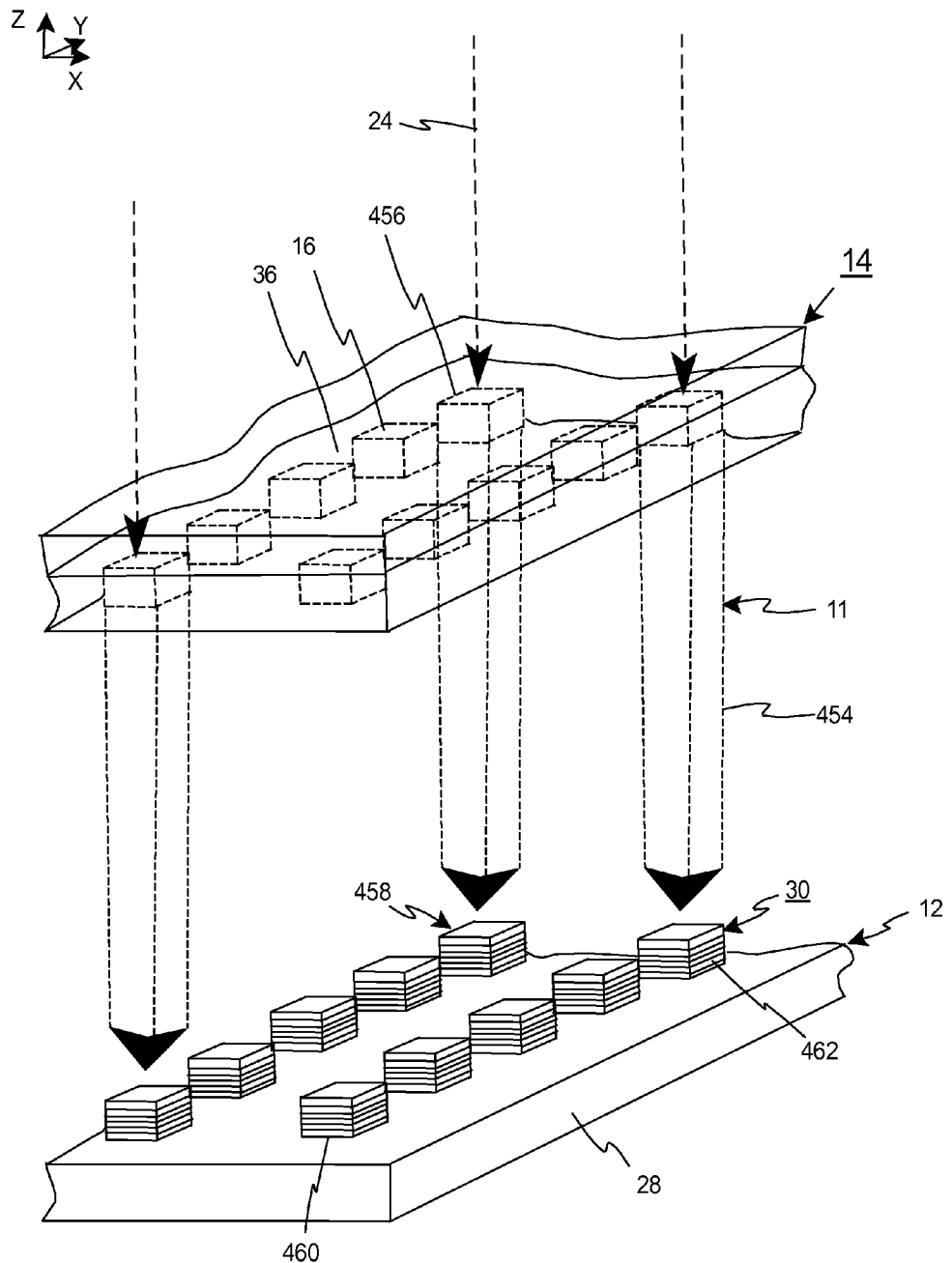
FIG. 4 is a simplified perspective view of a portion of the reticle and a portion of the workpiece.

FIG. 4 is a simplified perspective view of a portion of the reticle 14 including ten, spaced apart transmitting regions 16, and a portion of the workpiece 12 including a portion of the substrate 28 and ten, spaced apart, generally square, posts 30 that cantilever upward, away from the substrate 28. A portion of the shaped illumination beam 24 (long dashed lines with arrows) and a portion of the pattern of energy 11 (short dashed lines with arrows) are also shown in FIG. 4.

FIG. 4 also illustrates that at this particular moment, the shaped illumination beam 24 is shaped to be directed at and illuminate only three of the illustrated transmitting regions 16 (sometimes referred to as "targeted pixels 456"). With this design, at this moment, the shaped illumination beam 24 is only transmitted through the three targeted pixels 456, and the pattern of energy 11 includes three spaced apart shafts of light 454, with each shaft of light 454 being directed at a separate one of the posts 30 (sometimes referred to as "targeted posts 458"). In FIG. 4, there are three targeted posts 458, and each shaft of light 454 is generally rectangular shaped (because of the rectangular shape of each transmitting region 16) to correspond to the desired shape of the targeted post 458.

As provided above, each separate transmitting region 16 in the reticle 14 is available for independent adjustment of dose, by simply adding director elements 350 (illustrated in FIG. 3A) to or removing director elements 350 from the population of director elements 350 that are targeted at that targeted pixel 456 in the reticle 14. At the particular moment captured in FIG. 4, seven of the ten transmitting regions 16 receive no light (dosage=zero), while the three targeted pixels 456 receive a dosage of light. In this example, the size of the dosage received is adjustable by selectively adjusting the number of director elements 350 that direct the light at the respective targeted pixel 456. As alternative, non-exclusive examples, each of the three targeted pixels 456 that receive a dosage of light, can receive light that is reflected off of one, two, three, five or ten director elements 350.

It should be noted that although the shaped illumination beam 24 is illustrated in FIG. 4 as being parallel with the Z axis, in certain embodiments, the shaped illumination beam 24 can be directed at the targeted pixels 456 at an angle other that parallel with the Z axis. Further, the shaped illumination beam 24 can be easily adjusted with the director elements 350 to rapidly and accurately illuminate the desired targeted pixels 456 and illuminate the targeted posts 458.

As provided herein, in certain embodiments, each independent post 30 is a biomolecule "post" (e.g. a biosensor) that includes a plurality of layers 462 of biomolecules that are sequentially added to form the respective post 30. The number and composition of each of the layers 462 can be varied.

In one embodiment, the independent posts 30 can be constructed by first coating the workpiece 12 with a proprietary material containing 'captured' biomolecules. In one embodiment, during the forming of the first layer 462, selected post areas 460 of the workpiece 12 that correspond to the posts 30 are exposed by the imaging assembly 10 to excite and propagate a cross-linking of the biomolecule in the coated material with the existing material of the substrate 28 lying beneath it. In the case of exposing (illuminating) the first layer 462, the exposed coated material biomolecules in the coated material bind to the substrate 28 at the dedicated post areas 460 on the workpiece 12. In the case of the second layer 462 and all subsequent layers 462, the exposed (illuminated) coated material biomolecules are bound to the existing biomolecule stack at the location of each biosensor 30.

In certain BioTest chips 12, there are over four hundred separate exposure layers 462. These many exposure layers 462 vary only in terms of which subset of post patterns do not receive the pattern of energy 11. By selectively not exposing a post 30 at a given layer 462, the biomolecules that are within that layers' coated material will not be cross-linked to the existing stack, and thus be washed away during the cleaning step that follows each layers' 462 exposure. In this way, many millions of different 'biomolecule stack designs' can be constructed from existing materials and processes by changing which posts 30 are exposed for each layer 462. Stated in another fashion, the imaging assembly 10 provided herein is uniquely designed to be quickly adjusted to manufacture new and different BioTest chips 12. In one embodiment, the reticle 14 includes a plurality of reticle array areas (e.g. partial array areas having the transmitting regions 16 and the non-transmitting regions 36) on the reticle array 16. The imaging assembly 10 can expose (illuminate) one of the reticle array areas on the reticle array 16. As a result, the selected post areas 460 of the workpiece 12 that correspond to the reticle array area are exposed by the imaging assembly 10 to excite and propagate a cross-linking of the biomolecule. In one embodiment, the imaging assembly 10 includes a reticle stage that moves relative to the workpiece 12 and some of the other components of the imaging assembly 10. For example, a plurality of the reticles 14 having each different pattern is arranged on the reticle stage.

Figure 5:
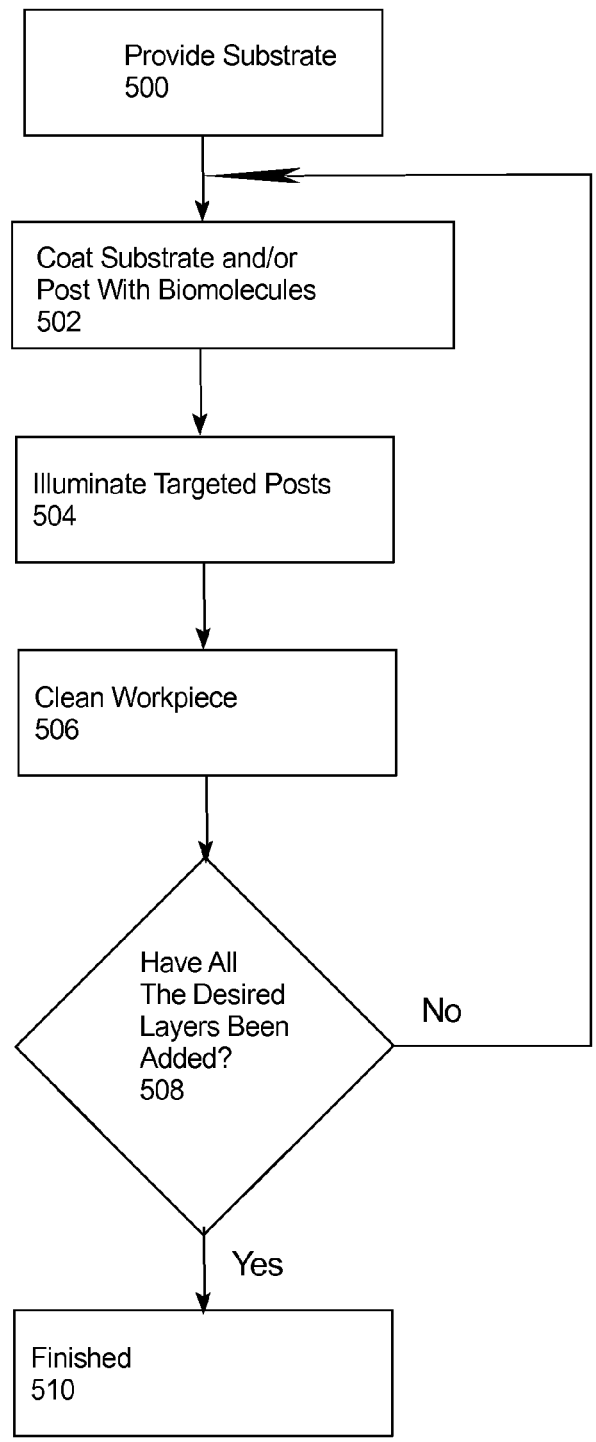
FIG. 5 is a flow chart that illustrates a method for manufacturing a workpiece having features of the present invention.

FIG. 5 is a flow chart that outlines a non-exclusive method for manufacturing a workpiece having features of the present invention. At block 500, the substrate 500 is provided. Subsequently, at block 502 the substrate is coated with the desired level of biomolecules. Next, at block 504, the targeted posts are illuminated. This can be performed by adjusting the director elements to shape the shaped illumination beam to target the desired targeted pixels in the reticle and illuminate the targeted posts with the pattern of energy. It should be noted that at block 504, that this layer of biomolecules will bond (cross-link) to the substrate or the previously bonded layer at the targeted (illuminated) posts, and will not bond (not cross-link) to the substrate or the posts that were not targeted (not illuminated).

Subsequently, at block 506, the workpiece is cleaned. At this time the unbonded portions of the layer of biomolecules will wash off. Next, at block 508, the question is asked if all of the desired layers have been added to all of the posts. If no, blocks 502-508 are repeated until the answer is yes. Finally, at block 510, the process is complete.

Figure 6:
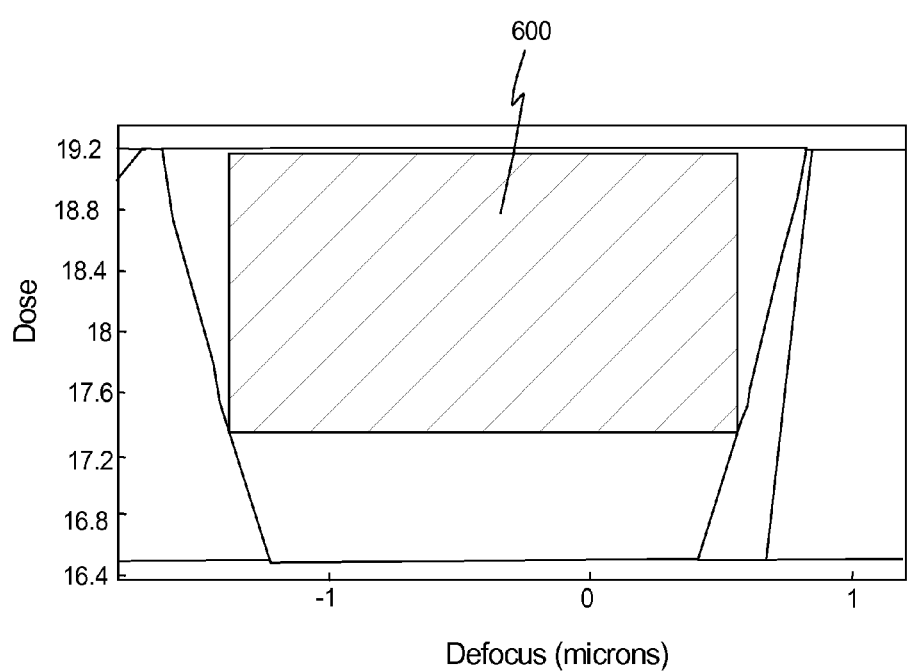
FIG. 6 illustrates an aerial image intensity distribution for a post.

FIG. 6 illustrates a process window for a one micron post generated by an aerial image intensity distribution using a KrF NA=0.5 incoherent imaging system. The illustrated result is a one micron post on a two micron pitch. The vertical axis shows dose (in mJ/cm^2), and the horizontal axis shows defocus (in microns). This result shows a wide available rectangular shaped process window 600 compared to currently available process methods (e.g. semiconductor manufacturing). In terms of imaging resolution and 'image integrity' (e.g. 'image contrast', 'normalized image log slope'), the simulations illustrate this incoherent imaging mode is easily capable of achieving a one micron 'post' resolution.

While the particular assembly as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An imaging assembly for directing a pattern of energy at a workpiece, the imaging assembly comprising:
   an illumination source that directs an illumination beam along an illumination beam path;
   a director assembly positioned along the illumination beam path, the director assembly including a plurality of director elements that are individually controlled to selectively adjust a shape of the illumination beam to provide a shaped illumination beam that is directed along a shaped beam path;

a reticle that is positioned along the shaped beam path, the reticle including a plurality of spaced apart, transmitting regions that are organized in a reticle array; wherein the shaped illumination beam that is transmitted through the transmitting regions defines the pattern of energy that is directed at the workpiece; and wherein the reticle array corresponds to a plurality of post areas on the workpiece; and a control system including a processor that individually controls each of the plurality of director elements to selectively adjust the shape of the shaped illumination beam.

2. The imaging assembly of claim 1 wherein the reticle array is two dimensional, and pattern of energy defines a plurality of spaced apart shafts of light that are directed at the workpiece.

3. The imaging assembly of claim 2 wherein each of the transmitting regions has a surface roughness so that the pattern of energy is incoherent.

4. The imaging assembly of claim 2 wherein each of the transmitting regions has a surface roughness is between approximately ten nanometer root mean square and ten micron root mean square.

5. The imaging assembly of claim 2 wherein each of the transmitting regions is generally rectangular in shape.

6. The imaging assembly of claim 2 wherein the workpiece includes a plurality of spaced apart posts that are arranged in a two dimensional post array, wherein the number of transmitting regions is equal to the number of posts, and wherein the size and shape of the reticle array corresponds to the size and shape of the post array.

7. The imaging assembly of claim 1 wherein the plurality of director elements are moved and positioned relative to the reticle and workpiece which are fixed.

8. An imaging assembly for directing a pattern of energy at a workpiece, the imaging assembly comprising:

an illumination source that directs an illumination beam along an illumination beam path;

a director assembly positioned along the illumination beam path, the director assembly including a plurality of director elements that are individually controlled to selectively adjust a shape of the illumination beam to provide a shaped illumination beam that is directed along a shaped beam path;

a reticle that is positioned along the shaped beam path, the reticle including a plurality of spaced apart, transmitting regions that are organized in a reticle array; wherein the reticle array is a two dimensional array; wherein the shaped illumination beam that is transmitted through the transmitting regions defines the pattern of energy that is directed at the workpiece, the pattern of energy includes a plurality of spaced apart shafts of light; wherein each of the transmitting regions has a surface roughness so that the pattern of energy is incoherent and a control system including a processor that individually controls each of the plurality of director elements to selectively adjust the shape of the shaped illumination beam.

9. The imaging assembly of claim 8 wherein each of the transmitting regions has a surface roughness is between approximately ten nanometer root mean square and ten micron root mean square.

10. The imaging assembly of claim 8 wherein the workpiece includes a plurality of spaced apart posts that are arranged in a two dimensional post array, and wherein the number of transmitting regions is equal to or greater than the number of posts areas, and wherein the size and shape of the reticle array corresponds to the size and shape of the post array.

11. The imaging assembly of claim 8 wherein the plurality of director elements are moved and positioned relative to the reticle and workpiece which are fixed.

12. A method of manufacturing a BioTest chip that includes a plurality of spaced apart biomolecule posts, the method comprising the steps of:

providing a substrate that includes a plurality of spaced apart post areas;

coating at least a portion of the substrate with a biomolecule layer; and illuminating the biomolecule layer near one or more of the post areas to bond the biomolecule layer to the substrate with a pattern of energy from an imaging assembly, the pattern of energy including a plurality of spaced apart shafts of light directed at the substrate, the imaging assembly having (i) an illumination source that directs an illumination beam along an illumination beam path; (ii) a director assembly positioned along the illumination beam path, the director assembly including a plurality of director elements that are individually controlled to selectively adjust a shape of the illumination beam to provide a shaped illumination beam that is directed along a shaped beam path; and (iii) a reticle that is positioned along the shaped beam path, the reticle including a plurality of spaced apart, transmitting regions that are organized in a reticle array; wherein the shaped illumination beam that is transmitted through the transmitting regions defines the pattern of energy that is directed at the substrate; and wherein the reticle array corresponds to the plurality of post areas on the substrate.

13. The method of claim 12 wherein the step of illuminating further includes the imaging assembly having a control system including a processor that individually controls each of the plurality of director elements to selectively adjust the shape of the shaped illumination beam and the pattern of energy.

14. The method of claim 13 wherein the step of illuminating includes the reticle array being two dimensional.

15. The method of claim 13 wherein the step of illuminating includes the transmitting regions having a surface roughness so that the pattern of energy is incoherent.

16. The imaging assembly of claim 1 wherein the director assembly includes a plurality of separate director arrays; and wherein the director arrays include the plurality of director elements.

17. The imaging assembly of claim 1 wherein the illumination source directs a pulsed beam as the illumination beam.

18. An imaging assembly for directing a pattern of energy at a workpiece, the imaging assembly comprising:

an illumination source that directs an illumination beam along an illumination beam path;

a director assembly positioned along the illumination beam path, the director assembly including a plurality of separate director arrays that selectively adjust a shape of the illumination beam to provide a shaped illumination beam that is directed along a shaped beam path;

a reticle that is positioned along the shaped beam path, the reticle including a plurality of spaced apart, transmitting regions that are organized in a reticle array; wherein the shaped illumination beam that is transmitted through the transmitting regions defines the pattern of energy that is directed at the workpiece; and a control system including a processor that individually controls each of the plurality of director arrays to selectively adjust the shape of the shaped illumination beam;

wherein the reticle array corresponds to a plurality of post areas on the workpiece.

19. The imaging assembly of claim 18 wherein each of the director arrays includes a plurality of director elements that are individually controlled to selectively adjust the shape of the illumination beam.

\* \* \* \* \*